United States Patent [19]

Guley et al.

[11] Patent Number: 5,095,151
[45] Date of Patent: Mar. 10, 1992

[54] PREPARATION OF PROPRANOLOL HYDROCHLORIDE MACROCRYSTALS

[75] Inventors: Paul C. Guley, Plattsburgh; James S. Farina, Rouses Point, both of N.Y.

[73] Assignee: American Home Products Corporation, New York, N.Y.

[21] Appl. No.: 736,619

[22] Filed: May 21, 1985

[51] Int. Cl.$^5$ .......................................... C07C 217/32
[52] U.S. Cl. .................................:............... 564/349
[58] Field of Search ................... 564/349; 260/501.18; 514/50, 957

[56] References Cited

U.S. PATENT DOCUMENTS

| | | | |
|---|---|---|---|
| 3,337,628 | 8/1967 | Crowther et al. | 564/349 |
| 3,410,901 | 11/1968 | Kunz et al. | 564/349 |
| 3,520,915 | 7/1970 | Crowther et al. | 260/501.18 X |
| 3,857,891 | 12/1974 | Holmes et al. | 564/349 |
| 4,138,475 | 2/1979 | McPingh et al. | 424/19 |
| 4,259,315 | 3/1981 | Lippmann et al. | 424/37 |
| 4,311,708 | 1/1982 | Manbury et al. | 564/349 X |
| 4,379,167 | 4/1983 | Lunsford et al. | 564/349 X |
| 4,460,605 | 7/1984 | Petrik et al. | 564/349 X |

*Primary Examiner*—Richard L. Raymond
*Attorney, Agent, or Firm*—Adley F. Mandel

[57] ABSTRACT

There is described a process for the preparation of high yields of propranolol hydrochloride having a particle size within the range of 420 to 1200 microns wherein the propanolol hydrochloride is recrystallized from, as a solvent, a mixture of n-propanol and heptane.

The propranolol hydrochloride macrocrystals are useful themselves in capsule pharmaceutical dosage forms and when coated with a sustained release coating composition, are useful in the manufacture of sustained action capsule and tablet pharmaceutical dosage.

4 Claims, 2 Drawing Sheets

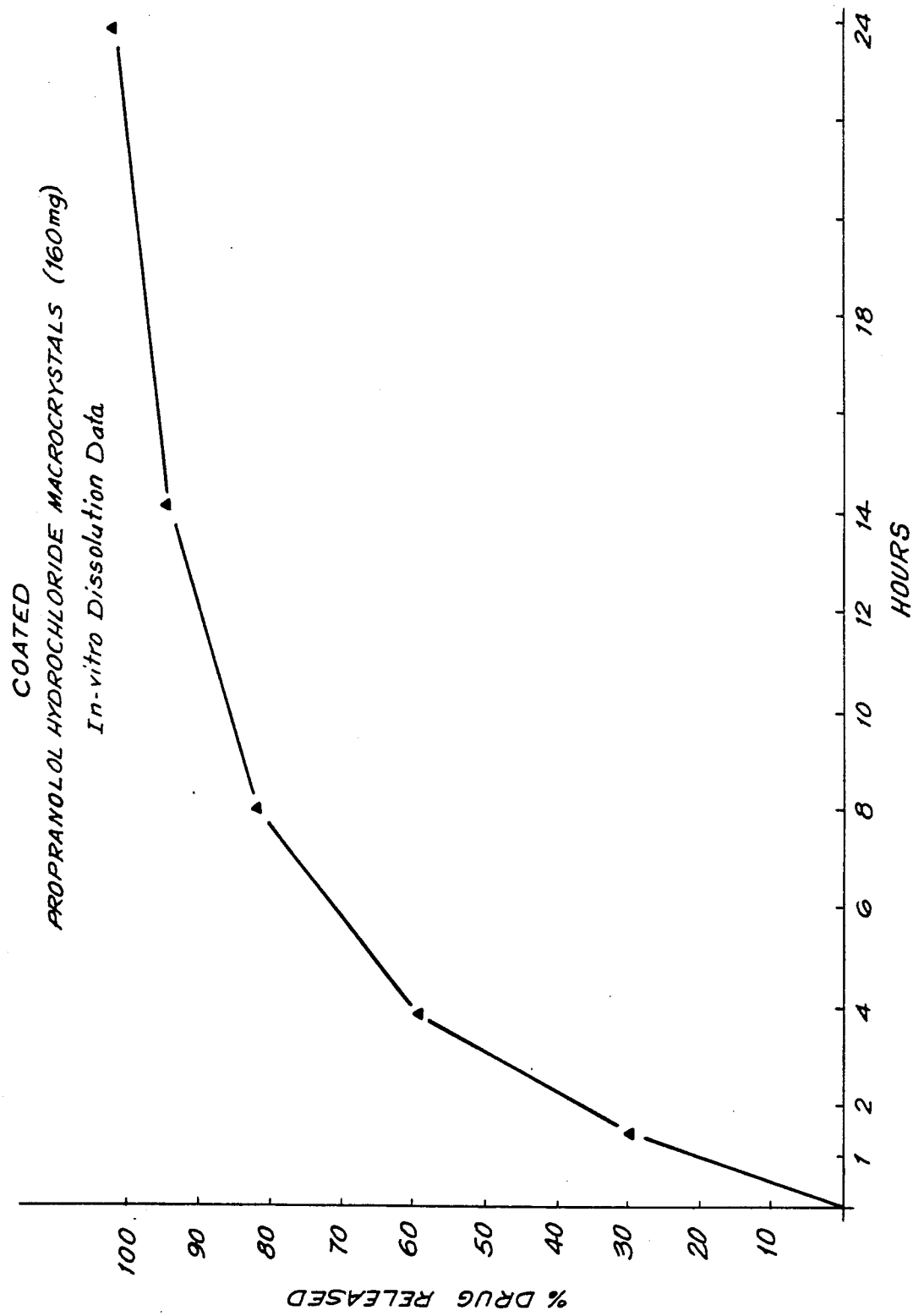

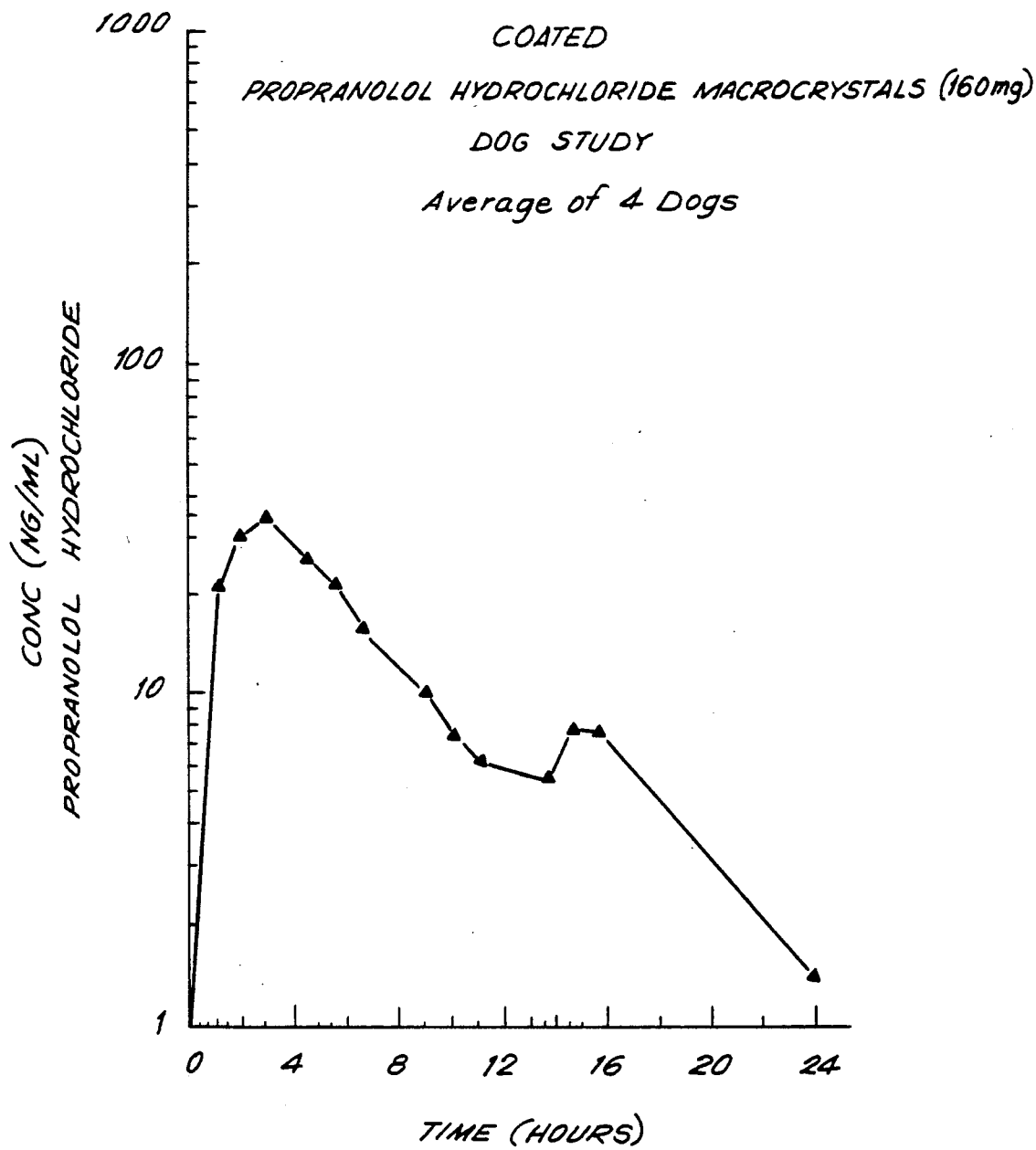

PREPARATION OF PROPRANOLOL HYDROCHLORIDE MACROCRYSTALS

BACKGROUND OF THE INVENTION

This invention relates to preparation of propranolol hydrochloride macrocrystals and more particularly to the preparation of high yields of propranolol hydrochloride macrocrystals having a particle size within the range of 420 to 1200 microns. The propranolol hydrochloride macrocrystals are useful in pharmaceutical capsule dosage forms, either uncoated, or coated to provide delayed or sustained release therapeutic preparations.

Propranolol hydrochloride is a well known pharmaceutical which has heretofore been marketed in tablet form and as sustained release encapsulated spheroids. See, for example, U.S. Pat. Nos. 3,337,628 and 4,138,475. In these pharmaceutical preparations, propranolol hydrochloride in powder form is utilized to form the tablets and spheroids. The propranolol hydrochloride is crystallized from solvents such as cyclohexane under conditions to provide crystalline material in the size range of 10 to 50 microns mean particle size depending on grade.

In forming tablets of propranolol hydrochloride powder, it is conventional to admix the active ingredient with excipients such that a small but accurate amount of active ingredient, i.e. 10 or 20 milligrams, may be slugged and formed into tablets weighing of the order of 105 to 120 milligrams.

Also in forming spheroids in accordance with U.S. Pat. No. 4,138,475 the propranolol hydrochloride powder is admixed with microcrystalline cellulose in order to form spheroids which are then film coated to provide sustained release dosage forms.

DESCRIPTION OF THE INVENTION

The present invention relates to the preparation of high yields of macrocrystals of propranolol hydrochloride having a particle size within the range of about 420 to 1200 microns wherein the propranolol hydrochloride is recrystallized from, as a solvent, a mixture of n-propanol and commercial grade heptane. More particularly the recrystallization is carried out after the propranolol hydrochloride in admixture with the n-propanol is refluxed with moderate stirring for from 1 to 5 hours.

More particularly, the present invention relates to the preparation of macrocrystals of propranolol hydrochloride having a particle size within the range of 420 to 1200 microns by suspending propranolol hydrochloride in n-propanol, heating the resulting slurry to solution and then concentrating the solution by distillation to a concentration of about 1 gram to about 2 grams of propranolol per milliliter of n-propanol. The concentrated mixture is refluxed under moderate agitation for an adequate period of time to permit crystal growth. Heptane is added to the refluxing mixture at such a rate as to maintain reflux in an amount approximately equal to the amount of n-propanol in the refluxing mixture. The solution is then cooled to 0° C. in from about 1 to 2 hours.

The macrocrystals of the present invention can be directly encapsulated in hard gelatin capsules in a conventional encapsulation machine similarly as the spheroids in U.S. Pat. No. 4,138,475. Also the macrocrystals of the present invention can be directly film coated as in U.S. Pat. No. 4,138,475 and then encapsulated to provide sustained release dosage forms. In the first instance, the steps and costs of admixing with excipients can be eliminated and in the second instance the steps and costs of admixing the propranolol hydrochloride with microcrystalline cellulose and spheronizing the admixture can be eliminated.

In particular, the macrocrystals of the present invention can be used to replace the uncoated spheroids or the powder admixture utilized as the loading dose and/or the uncoated spheroids used for further coating in the copending applications of Paul C. Guley U.S. Ser. No. 730,926 filed May 6, 1985 and Atul M. Mehta et al U.S. Ser. No. 731,175 filed May 6, 1985, both entitled "Formulations Providing Three Distinct Releases" the disclosures of which are incorporated herein in their entirety by reference.

DETAILED DESCRIPTION OF THE INVENTION

Selection of a proper solvent is critical to obtaining the macrocrystals of this invention. For example, it is possible to recrystallize propranolol hydrochloride from methanol such that the majority of the particles are larger than 595 microns, with up to 44% between 1000-595 microns in size. Microscopic examination of the 1000-595 micron sized propranolol hydrochloride showed them to be multi-faceted crystals. Unfortunately, these many faced crystals are unsuitable for developing an effective sustained release dosage form. An alternate recrystallization system is also needed for practical reasons. Crystallization of propranolol hydrochloride from methanol at high concentrations yields very thick slurries. Such slurries are very difficult to remove from process kettles.

Similarly concentrated solutions (2 grams per milliliter) propranolol hydrochloride in heated n-propanol were prepared. The heterogeneous mixtures were then moderately stirred at reflux for specified times, cooled, and the solids isolated. In all cases, the recoveries of product were very high.

A very high proportion (41.4%) of 1000-595 microns sized propranolol hydrochloride was isolated when the concentrated propanol mixture was refluxed for three hours. The distribution of crystals in this size range decreased to 33.7% when the precipitated propranolol hydrochloride was only refluxed one hour. Upon extending the crystal growing time, the percentage of 1000-595 micron crystals dropped to 25.8% while the relative amount of particles ≧1000 microns increased to 46.2%. Shortening the cooling time improved the percentage of desirable sized crystals. However, the original distribution was approached when rapid stirring was employed during an extended reflux period and shortened cooling time.

Although good crystal size distributions were observed, the problem of removing the propranolol hydrochloride from the process kettle remained. In practice, it is very difficult to remove thick slurries of solids, as obtained above, from process vessels.

In accordance with this invention, the addition of heptane as a co-solvent to the crystallization medium provided suitable macrocrystals and in addition permitted removal of the recrystallization solution from the process vessel.

EXAMPLE 1

Concentrated propranolol hydrochloride mixtures were prepared by suspending the propranolol hydrochloride in n-propanol, heating to solution, then distilling off the solvent until a concentration of 2 g/ml was attained. The resulting mixtures were then refluxed three hours under moderate agitation to allow for crystal growth. Next, a volume of commercial grade heptane equal to the volume of n-propanol in the concentrate (final concentration = 1 g propranolol hydrochloride per ml solvent system) was added at such a rate as to maintain reflux. The remaining slurries were either cooled to 0° C., or heated at reflux, then cooled to 0° C. prior to isolating the crystals by filtration. The results are shown in the following Table I.

Upon preparing a n-propranol/heptane mixture of propranolol hydrochloride as described above, followed by cooling (Run 1, Table I), a favorable crystal size distribution was observed. When the residence time at room temperature was eliminated, and the hot, heterogeneous mixture was cooled to 0° C. over one hour (Run 2, Table I), the population of the 1000-595 micron crystals dropped to 31.3%. On the other hand, a faster cooling rate (Run 3, Table I) improved the percentage of propranolol hydrochloride between 1000-595 microns. A four hour reflux period, coupled with a one hour cooling rate, gave more desirable results than a three hour reflux time and a one hour cooling rate (cf. Runs 4 to 2, Table I), but less desirable results than Run 3.

A significant increase in the large (>1000 microns) particle size distribution, along with a 31.3% growth in the 1000-595 micron range, was observed (cf. Runs 5 to 2, Table I) upon refluxing the propranolol hydrochloride/n-propranol/heptane mixture for 1.17 hours. The percentage of large crystals, to the detriment of the 1000-595 micron ones, rose even further when a two hour reflux was employed (Run 6, Table I). Utilization of a rapid stirring rate while refluxing the aforementioned heterogeneous mixture for one hour shifted the size distribution toward the smaller crystals (Run 7, Table I).

No major change in the crystal size distribution was seen when the propranolol hydrochloride concentrate was heated for only one hour in n-propanol (cf. Runs 8 to 5, Table I). Immediate addition of heptane to the n-propanol concentrate (without a reflux period), coupled with the use of a more dilute mixture (Run 9, Table I), also produced little change in the 1000-595 micron population. However, a 16.9% rise in the 1000-595 micron sized crystals and a significant reduction in the proportion of >1000 microns occurred upon using an even more dilute propranolol hydrochloride/n-propanol/heptane mixture (cf. entries 10 to 9, 8, 5, Table I).

In the following Table I, all reaction mixtures were first concentrated to 2 grams of propranolol hydrochloride per milliliter of n-propanol prior to initial stirring at 96° C. except that in Run 9 the initial concentration was 1.67 grams propranolol hydrochloride per milliliter n-propanol and in Run 10 the initial concentration was 1.43 grams per milliliter. Stirring was at a moderate rate except in Run 7 wherein a rapid stirring rate was employed.

In column 2, the first entry (temperature and time) is for crystal growing conditions, the second entry, which is in brackets, represents the heptane addition conditions and the third and subsequent entries represent the cooling conditions. In each run, heptane was added at a rate so as to maintain reflux. The volume of heptane added equals the volume of n-propanol in the initial concentration. The final concentration is 1 gram propranolol hydrochloride per milliliter of solvent mixture. In Runs 5 through 10, during the crystal growing conditions, the n-propanol/heptane 1:1 mixture was maintained for the second indicated reflux period at a concentration of 1 gram propranolol hydrochloride per milliliter of solvent mixture.

TABLE I

| | Crystallization from n-Propanol/Heptane | | | | | | |
|---|---|---|---|---|---|---|---|
| | Crystallization | Percent | Crystal Size (microns) Distribution (%) | | | | |
| Run | Temp(°C.)/Time(h) | Recovery | ≧1000 | ≧595 | ≧420 | ≧250 | ≧250 |
| 1 | 96/3<br>[97-81/0.27]<br>81-rt/0.5<br>rt/15.75<br>21-1/0.25<br>0-5/0.5 | 98.2 | 28.3 | 36.7 | 17.2 | 12.5 | 4.9 |
| 2 | 96/3<br>[96-85/0.25]<br>85-4/1.05<br>0-5/0.5 | 98.9 | 5.2 | 31.3 | 30.3 | 25 | 6.1 |
| 3 | 96/3<br>[96-85/0.25]<br>85-5/0.13<br>0-5/0.5 | 98.5 | 11.2 | 42.8 | 25.2 | 15.1 | 3.6 |
| 4 | 96/4<br>[96-85/0.33]<br>85-3/1<br>0-5/0.5 | 96.3 | 23.6 | 34.3 | 18.5 | 13.4 | 9.4 |
| 5 | 96/3<br>[96-85/0.25]<br>[85/1.17]<br>85-5/1<br>0-5/0.5 | 98.2 | 45.5 | 41.1 | 7.8 | 3.8 | 0.6 |
| 6 | 96/3<br>[96-85/0.25]<br>[85/2]<br>85-5/0.75<br>0-5/0.5 | 98.7 | 57.7 | 31.8 | 6.3 | 3.2 | 1 |
| 7 | 96/3 | 99.1 | 8.7 | 21.7 | 13.5 | 22.9 | 29.5 |

TABLE I-continued

| | Crystallization from n-Propanol/Heptane | | | | | |
|---|---|---|---|---|---|---|
| Run | Crystallization Temp(°C.)/Time(h) | Percent Recovery | Crystal Size (microns) Distribution (%) | | | |
| | | | ≧1000 | ≧595 | ≧420 | ≧250 | ≧250 |
| 8 | [96–850/0.25]<br>[85/1]<br>85–5/1<br>0–5/0.5<br>96/1<br>[96–85/0.25]<br>[85/1]<br>85–5/1<br>0–5/0.5 | 99 | 44.4 | 40.9 | 8.1 | 3 | 0.7 |
| 9 | 96/0.0<br>[96–85/0.38]<br>[85/1]<br>85–5/1<br>0.5/0.66 | 98.8 | 36.5 | 40.6 | 8.9 | 7.7 | 5.7 |
| 10 | 96/0.0<br>[96–85/0.42]<br>[85/1]<br>85–5/0.92<br>0–5/0.5 | 99.1 | 13.1 | 47.8 | 16.3 | 15.4 | 6.8 |

Based on the above work, two equal sized pilot plant runs were performed under conditions similar to those used in entry 8, Table I. A total of 39.7 kg of macrocrystalline propranolol hydrochloride (Table II) was produced.

TABLE II

| Batch No. | Yield (%) | Crystal Size (microns) Distribution (%) | | | | |
|---|---|---|---|---|---|---|
| | | ≧1000 | ≧595 | ≧420 | ≧250 | ≧250 |
| AQK | 100 | 35.4 | 41.3 | 9.6 | 7.0 | 5.9 |
| ARL | 98.5 | 19.6 | 37.8 | 17.5 | 14.1 | 10.5 |

Thus in accordance with this invention, a method has been developed for preparing macrocrystalline propranolol hydrochloride that is suitable for pharmaceutical dosage formulation.

EXAMPLE 2

Propranolol hydrochloride macrocrystals in the amount of 19.876 kilograms from Batch No. AQK were screened through a #8 screen to remove two kilograms of agglomerated chunks and of the remaining 17.876 kilograms, three 5 gram samples were put through a Sonic Sifter and a 100 gram sample was put through a Ro-Tap screen. The results appear in Table III.

TABLE III

| Sonic Sifter Data | | | Ro-Tap Data | |
|---|---|---|---|---|
| Retained on Screen | Screen Range (μ) | (%) n = 3 | Screen Range (μ) | (%) n = 1 |
| 16 | 2360–1180 | 17 | 2360–1190 | 24 |
| 18 | 1180–1000 | 12 | 1190–1000 | 16 |
| 20 | 1000–841 | 20 | 1000–841 | 14 |
| 30 | 841–595 | 22 | 841–595 | 24 |
| 40 | 595–425 | 11 | 595–420 | 9 |
| 60 | 425–250 | 9 | 420–250 | 6 |
| Pan | 250–0 | 9 | 250–0 | 7 |

Dissolution differences for the different size macrocrystals were slight. Differences were noted at the 5 minute assay point with all drug dissolved between 10 and 15 minutes. The method was USP I, 50 rpm in one liter of water at 37° C.

Light microscope photographs at 6× and electron microscope photographs at the lowest magnification 30× defines the crystal habits as a function of particle size.

Two basic types of habits were noted. Unfinished rectangular octahedrons were more prevalent in the larger size macrocrystals. Agglomerates of odd shaped octahedrons and other crystals were distributed throughout the particle size range but more prevalent in the macrocrystals smaller than 30 mesh.

A blend of 16–30 mesh propranolol hydrochloride macrocrystals in the amount of 3000 grams was placed in a Glatt fluid bed coater. A film formulation consisting of 90 grams of ethylcellulose (Dow-Ethocell N-50) and 10 grams if hydroxypropyl methylcellulose (Shin - Etsu - Pharmacoat 606) dissolved in 3 liters of one-half methanol and one-half methylene chloride was sprayed at an average flow rate of about 48 mls per minute over 100 minutes. At the conclusion of the coating process, the coated macrocrystals were air dried. They were then filled into hard gelatin capsules using a conventional encapsulation machine such that the capsule contained 160 mg of propranolol hydrochloride. There was thus obtained a sustained release composition containing propranolol hydrochloride in which the film coat represents about 3% by weight of the propranolol hydrochloride.

The encapsulated coated propranolol hydrochloride macrocrystals were tested for in vitro drug release and for in vivo bioavailability in dogs.

FIG. 1 represents the dissolution profile of the 160 mg propranolol hydrochloride containing 3% coated macrocrystals of this Example 2. The in vitro dissolution method was USP I, 100 rpm in 0.9 liter of USP gastric fluid at 37° C. for 1.5 hours then the dissolution media was changed to pH 6.8 buffered water for the remaining 24 hours of dissolution.

FIG. 2 represents the average in vivo profile of coated propranolol hydrochloride macrocrystals in four different dogs dosed once a day with a 160 mg of propranolol hydrochloride 3% coated macrocrystals of this Example 2. The area under the curve is 217 ng. hs/ml (0–13.5 hours).

Variations can be made in the coating weight and composition of this Example 2. For example, the weight percent of coating composition to propranolol hydrochloride can vary from about 1.75 to 5 percent. Also, the coating composition can vary as described in the copending applications of Guley and Mehta et al described above. Thus in the copending application of Guley U.S. Ser. No. 730,926, filed May 16, 1985, the propranolol macrocrystals can be coated with the pH sensitive coating composition described in the example of that application and in the examples of the Mehta et al application U.S. Ser. No. 731,175, filed May 6, 1985 and with the double coat compositions described in the Mehta et al application U.S. Ser. No. 731,175, filed May 6, 1985.

These coated propranolol hydrochloride macrocrystals of this invention surprisingly can be formulated to be compressed on a tablet machine and still provide sustained release propranolol hydrochloride without membrane rupture.

Hence the propranolol hydrochloride macrocrystals can be used in forming the press coated tablet described in Guley application U.S. Ser. No. 730,926, filed May 16, 1985. Also the propranolol hydrochloride macrocrystals can be used to form the sustained release tablets described in Guley et al U.S. Pat. Nos. 4,309,404; 4,309,405, 4,309,406; 4,248,856; 4,248,857 and 4,248,858.

We claim:

1. A method for the preparation of high yields of macrocrystals of propranolol hydrochloride having a particle size within the range of about 420 to 1200 microns which comprises recrystallizing propranolol hydrochloride from a heated solution of propranolol hydrochloride in as a solvent an admixture of n-propanol and heptane.

2. The method of claim 1 wherein the propranolol hydrochloride containing solution is refluxed from 1 to 5 hours and then cooled.

3. A method for the preparation of macrocrystals of propranolol hydrochloride having a particle size within the range of 420 to 1200 microns which comprises suspending propranolol hydrochloride in a solvent consisting essentially of n-propanol, heating the resulting slurry to solution, concentrating the solution by distillation to a concentration of about 1 gram to about 2 grams of propranolol per milliliter of n-propanol, refluxing the solution under moderate agitation for an adequate period of time to permit crystal growth, adding heptane to the refluxing solution at such a rate as to maintain reflux in an amount approximately equal to the amount of n-propanol in the refluxing solution, and cooling the solution to 0° C. in from about 1 to 2 hours.

4. The method of claim 3 wherein the propranolol hydrochloride containing solution is refluxed for from 1 to 5 hours.

* * * * *